US006891079B2

(12) United States Patent
Koenig et al.

(10) Patent No.: US 6,891,079 B2
(45) Date of Patent: *May 10, 2005

(54) WIPE

(75) Inventors: David W. Koenig, Menasha, WI (US); Lisa M. Kroll, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 230 days.

This patent is subject to a terminal disclaimer.

(21) Appl. No.: 10/029,404

(22) Filed: Dec. 20, 2001

(65) Prior Publication Data

US 2003/0118475 A1 Jun. 26, 2003

(51) Int. Cl.⁷ .................. A61F 13/15; A61F 13/20; A61L 9/00; A01N 25/34
(52) U.S. Cl. .................. 604/360; 604/289; 422/32; 424/404
(58) Field of Search .................. 604/359, 360, 604/290

(56) References Cited

U.S. PATENT DOCUMENTS

| | | | |
|---|---|---|---|
| 4,100,324 A | 7/1978 | Anderson et al. | |
| 4,167,559 A | 9/1979 | Michel | |
| 4,657,766 A | 4/1987 | Goodall | |
| 4,772,479 A | 9/1988 | Goodall | |
| 4,798,603 A | 1/1989 | Meyer et al. | |
| 4,828,860 A | 5/1989 | Goodall | |
| 5,017,562 A | 5/1991 | Holmes et al. | |
| 5,139,779 A | 8/1992 | McNeff | |
| 5,176,668 A | 1/1993 | Bernardin | |
| 5,176,672 A | 1/1993 | Bruemmer et al. | |
| 5,192,606 A | 3/1993 | Proxmire et al. | |
| 5,279,838 A | 1/1994 | McNeff | |
| 5,306,487 A | 4/1994 | Karapasha et al. | |
| 5,364,382 A | 11/1994 | Latimer et al. | |
| 5,482,765 A | 1/1996 | Bradley et al. | |
| 5,486,166 A | 1/1996 | Bishop et al. | |
| 5,490,846 A | 2/1996 | Ellis et al. | |
| 5,507,250 A | 4/1996 | Reddy et al. | |
| 5,509,915 A | 4/1996 | Hanson et al. | |
| 5,518,750 A | 5/1996 | Mcneff | |
| 5,525,346 A | 6/1996 | Hartung et al. | |
| 5,723,149 A | 3/1998 | Bonte et al. | |
| 5,797,891 A | 8/1998 | Wiersma | |
| 5,800,818 A | 9/1998 | Prugnaud et al. | |
| 5,843,056 A | 12/1998 | Good et al. | |
| 5,860,391 A | 1/1999 | Maxwell et al. | |
| 5,879,341 A | 3/1999 | Odorzynski et al. | |
| 5,906,825 A | 5/1999 | Seabrook, Jr. et al. | |
| 5,932,495 A | 8/1999 | Boney et al. | |
| 6,057,372 A | 5/2000 | Nobuhiro et al. | |
| 6,063,382 A | 5/2000 | Nakajima et al. | |
| 6,159,487 A | * 12/2000 | Znaiden et al. .............. 424/402 |
| 6,228,265 B1 | * 5/2001 | Henderson | |
| 6,309,736 B1 | 10/2001 | McCormack et al. | |
| 6,338,855 B1 | 1/2002 | Albacarys et al. | |
| 6,485,734 B1 | 11/2002 | Baker et al. | |
| 2002/0119173 A1 | 8/2002 | Lin et al. | |
| 2002/0136755 A1 | 9/2002 | Tyrrell et al. | |
| 2003/0035785 A1 | 2/2003 | Palumbo et al. | |
| 2003/0105445 A1 | 6/2003 | Lange et al. | |
| 2003/0120228 A1 | * 6/2003 | Koenig et al. .............. 604/367 |

FOREIGN PATENT DOCUMENTS

| | | | | |
|---|---|---|---|---|
| EP | 0 565 266 B1 | 1/1999 | | |
| EP | 0 776 760 B1 | 5/1999 | | |
| EP | 0 922 457 A1 | * 6/1999 | .......... A61K/31/23 |
| JP | 4016163 A2 | 1/1992 | | |
| JP | 4074105 A2 | 3/1992 | | |
| JP | 7149608 A2 | 6/1995 | | |
| JP | 8019595 A2 | 1/1996 | | |
| JP | 8119872 A2 | 5/1996 | | |
| JP | 9187229 A2 | 7/1997 | | |
| JP | 9328410 A2 | 12/1997 | | |
| JP | 10045566 A2 | 2/1998 | | |
| JP | 11147818 A | 6/1999 | | |
| JP | 11200245 A2 | 7/1999 | | |
| JP | 11322630 A2 | 11/1999 | | |
| JP | 2000169320 A | 6/2000 | | |
| JP | 2001039812 A | 2/2001 | | |
| KR | 218093 | 10/1999 | | |
| WO | WO 96/41528 A1 | 12/1996 | | |
| WO | WO 99/20258 A1 | 4/1999 | | |
| WO | WO 01/95726 A1 | 12/2001 | | |
| WO | WO 02/51358 A2 | 7/2002 | | |

OTHER PUBLICATIONS

Facey, P.C. et al., Investigation of Plants Used in Jamaican Folk Medicine for Anti–Bacterial Activity, J. Pharm. Pharmacol., (1999), pp. 1455–1460, vol. 51:12.

Farrington, E., Diaper Dermatitis, Pediatric Nursing, (1992), pp. 81–82, vol. 18:1.

Gnan, S.O. et al., Inhibition of *Staphylococcus aureus* by aueous Goiaba Extracts, Journal of Ethnopharmacology, (1999), pp. 103–108, vol. 68.

Janniger, C.K. et al., Diaper Dermatits: An Approach to Prevention Employing Effective Diaper Care, Cutis, (1993), pp. 153–155, vol. 52.

Li, X–C et al., Antifungal Jujubogenin Saponins from *Colubrina retusa*, J. Nat. Prod., (1999), pp. 674–677, vol. 62:5.

Miyakoshi, M. et al., Antiyeast Steroidal Saponins from *Yucca schidigera* (Mohave Yucca), A New Anti–Food–Deteriorating Agent, J. Nat. Prod., (2000), pp. 332–338, vol. 63:3.

Nostro, A. et al., Extraction Methods and Bioautography for Evaluation of Medicinal Plant Antimicrobial Activity, Letters in Applied Microbiology, (2000), pp. 379–384, vol. 30.

(Continued)

Primary Examiner—Karin Reichle
(74) Attorney, Agent, or Firm—Senniger Powers

(57) ABSTRACT

A method of inhibiting production of ammonia from urine held adjacent a user's skin by an article. The method includes applying a composition including a *Yucca* sp. extract to an area of the wearer's skin. A wipe for wiping surfaces including a flexible sheet and a composition held by the sheet including a *Yucca* sp. extract.

6 Claims, No Drawings

OTHER PUBLICATIONS

Papadopoulou K. et al., Compromised Disease Resistance in Saponin–Deficient Plants. Proceedings of the National Academy of Scienes of the U.S.A., (1999), pp. 12923–12928, vol. 96:22.

Sires, U.I. et al., Diaper Dermatitis, How to Treat and Prevent, Postgraduate Medicine, (1995), pp. 79–84, vol. 98:6.

Van Setten, D.C. et al., Molecular Structures of Saponins from *Quillaja Saponaria* Molina, Advances in Experimental Medicine and Biology, (1996), pp. 185–193, vol. 404.

Wong, D.L. et al., Diapering Choices: A Critical Review of the Issues, Pediatric Nursing, (1992), pp. 41–54, vol. 18:1.

Yucca schidigera printout from Geocite Website.

Wallace, et al., Abstract of "Influence of Yucca Shidigera Extract on Ruminal Ammonia Concentrations and Ruminal Microorganisms", Appl Environ Microbiol, Jun. 1994, pp. 1762–1767, vol. 60, Issue 6, Rowett Research Institute, Bucksburn, Aberdeen, United Kingdom, PMID 8031077, UI 94304158.

Tanako, et al., Abstract of "Application of Saponins in Foods and Cosmetics: Saponins of Mohave Yucca and Sapindus Mukurossi", Adv Exp Med Biol, 1996, pp. 1–11, vol. 405, Suzugamine Women's College, Hiroshima, Japan, PMID 8910691, UI 97067277, Bibliographical Data.

Fiers, Sheila A., "Breaking the Cycle: The Etiology of Incontinence Dermatitis and Evaluating and Using Skin Care Products", Ostomy/Wound Management, The Journal for Extended Patient Care Management, Apr. 1996, pp. 32–43, vol. 42, No. 3, USA.

Yeo, et al., Abstract of "Effect of Feeding Diets Containing an Antibiotic, a Probiotic, or Yucca Extract on Growth and Intestinal Urease Activity in Broiler Chicks", Poult Sci, Feb. 1997, pp. 381–385, vol. 76, Issue 2, Department of Animal Science, Cheji National University, Republic of Korea, PMID 9057222, UI 97210047.

Lowe, et al., Abstract of "The Ameliorating Effect of Yucca Schidigera Extract on Canine and Feline Faecal Aroma", Res Vet Sci, Jul.–Aug. 1997, pp. 61–66, vol. 63, Issue 1, Gilbertson and Page Ltd., Welwyn Garden City, USA, PMID 9368958, UI 98035433.

Lowe, et al., Abstract of "The Effect of Yucca Schidigera Extract on Canine and Feline Faecal Volatiles Occurring Concurrently with Faecal Aroma Amelioration", Res Vet Sci, Jul.–Aug. 1997, pp. 67–71, vol. 63, Issue 1, Gilbertson and Page Ltd., Welwyn Garden City, USA, PMID 9368959, UI 98035434.

Sen, et al., Abstract of "Effect of Quillaja Saponaria Saponins and Yucca Schidigera Plant Extract on Growth of *Escherichia Coli*", Lett Appl Microbiol, Jul. 1998, pp. 35–38, vol. 27, Issue 1, Institute for Animal Production in the Tropics and Subtropics, University of Hohenheim, Stuttgart, Germany, PMID 9722995, UI 98390235.

* cited by examiner

WIPE

BACKGROUND OF THE INVENTION

The present invention relates generally to wipes and more particularly to a wipe containing a urease inhibitor to reduce production of ammonia from urine.

Diaper rash is caused by several factors, one of which is prolonged exposure to moisture. Moisture is conducive to bacteria growth and promotes skin maceration and breakdown which allows the bacteria to infect the damaged skin. The occasional presence of feces which can include vast numbers of organisms further increases the potential for bacterial and fungal infection of damaged skin. Further, some bacteria produce ammonia through degradation of urine. Ammonia is used as a nutritional substrate by bacteria, resulting in growth of more bacteria and production of more ammonia in an increasing detrimental cycle. The production of ammonia also raises the pH of the skin. Normal skin pH is between about 4 and about 6.8. This range tends to inhibit bacterial growth. As pH increases, bacterial growth increases. Further, some enzymes contained in feces such as lipases and proteases which damage skin are more active at high pH. The skin can also be damaged by an increase in pH. Thus, the production of ammonia causes several detrimental effects which can lead to diaper rash.

Increases in ammonia also increase offensive odors which can be embarrassing particularly for incontinent adults. Thus, reduction of ammonia production from urine is advantageous for several reasons. Accordingly, there is a need for a wipe or other preparation which reduces production of ammonia.

SUMMARY OF THE INVENTION

Briefly, a method of this invention inhibits production of ammonia from urine held adjacent a user's skin by an article. The method comprises applying a composition to an area of the wearer's skin. The composition includes a *Yucca* sp. extract.

In another aspect, a wipe of the present invention comprises a flexible sheet and a composition held by the sheet including a *Yucca* sp. extract.

Other features of the present invention will be in part apparent and in part pointed out hereinafter.

DETAILED DESCRIPTION OF THE PREFERRED EMBODIMENT

In accordance with the present invention, it has been discovered that compositions containing a *Yucca* sp. extract (hereinafter *yucca* extract), and more particularly *Yucca schidigera* are highly effective urease inhibitors (i.e., substances which inhibit production of ammonia from urine) when the compositions are applied directly to the skin or incorporated into a substrate such as a woven or non-woven material and used as a wipe.

The compositions of the present invention can be incorporated into a wet wipe, hand wipe, household wipe, industrial wipe and the like having an improved ability to inhibit production of ammonia from urine. Materials suitable for the substrate of the wet wipe are well known to those skilled in the art, and are typically made from a fibrous sheet material which may be either woven or nonwoven. For example, the wet wipes incorporating the ammonia inhibiting compositions of the present invention may include nonwoven fibrous sheet materials which include meltblown, coformed, air-laid, bonded-carded web materials, hydroentangled materials, and combinations thereof. Such materials can comprise synthetic or natural fibers, or a combination thereof. Typically, wet wipes have a basis weight of between about 25 grams per square meter and about 120 grams per square meter and desirably between about 40 grams per square meter and about 90 grams per square meter.

In one embodiment, the wet wipes incorporating the ammonia inhibiting compositions of the present invention comprise a flexible sheet such as a coformed basesheet of polymeric microfibers and cellulosic fibers having a basis weight between about 60 grams per square meter and about 80 grams per square meter and desirably about 75 grams per square meter. Such coformed basesheets are manufactured generally as described in U.S. Pat. No. 4,100,324, which is hereby incorporated by reference. Typically, such coformed basesheets comprise a gas-formed matrix of thermoplastic polymeric meltblown microfibers (e.g., polypropylene microfibers) and cellulosic fibers (e.g., wood pulp fibers).

The relative percentages of the polymeric microfibers and cellulosic fibers in the coformed basesheet can vary over a wide range depending upon the desired characteristics of the wet wipes. For example, the coformed basesheet may comprise between about 20 weight percent and about 100 weight percent, desirably between about 20 weight percent and about 60 weight percent, and more desirably between about 30 weight percent and about 40 weight percent of the polymeric microfibers based on the dry weight of the coformed basesheet being used to provide the wet wipes.

Alternatively, the wet wipes incorporating the ammonia inhibiting compositions of the present invention may comprise a flexible sheet such as a composite including multiple layers of materials. For example, the wet wipes may include a three layer composite including an elastomeric film or meltblown layer between two coformed layers as described above. In such a configuration, the coformed layers may define a basis weight between about 15 grams per square meter and about 30 grams per square meter and the elastomeric layer may include a film material such as a polyethylene metallocene film.

As previously mentioned, the wet wipes contain an urease inhibiting composition which is absorbed into the wet wipes. The amount of solution contained within each wet wipe may vary depending upon the type of material being used to provide the wet wipe, the type of solution being used, the type of container being used to store the wet wipes, and the desired end use of the wet wipes. Generally, each wet wipe contains between about 150 weight percent and about 600 weight percent and desirably between about 250 weight percent and about 450 weight percent solution based on the dry weight of the wipe for improved wiping. In one particular embodiment, in which the wet wipes are made from a coformed material comprising between about 30 weight percent and about 40 weight percent polymeric microfibers based on the dry weight of the wipe, the amount of solution contained within the wet wipe is between about 300 weight percent and about 400 weight percent and desirably about 330 weight percent based on the dry weight of the wet wipe. If the amount of solution is less than the above-identified range, the wet wipe may be too dry and may not adequately perform. If the amount of solution is greater than the above-identified range, the wet wipe may be oversaturated and soggy and the solution may pool in the bottom of the container holding the wet wipes.

The urease inhibiting solution incorporated into the wet wipes should contain an amount of *yucca* extract sufficient to provide urease inhibiting activity. A suitable amount of *yucca* extract is at least about 0.001 weight percent, and more desirably at least about 0.01 weight percent based on the total weight of the solution. Further, the amount of *yucca* extract should be small enough to prevent undesirable coloration of the solution. Desirably, the amount of *yucca* extract is less than about 1.0 weight percent based on total weight of the solution. Although other *yucca* extracts may be used without departing from the scope of the present invention, in one embodiment the *yucca* extract comprises *Yucca schidigera*, and more particularly, a *Yucca schidigera* solution sold under the trade designation *Yucca* 70 by Sher-Mar Enterprises of Poway, Calif.

The urease inhibiting solution of the present invention which is incorporated into the wet wipes may also contain a variety of other components which may assist in providing the desired wiping and urease inhibiting properties. For example, the components may include water, emollients, other surfactants, preservatives, chelating agents, pH buffers, fragrances, urease inhibiting actives, or combinations or mixtures thereof. The solution may also contain lotions and/or medicaments. To provide reduced skin irritation, the solution desirably includes at least about 80 weight percent water and more desirably at least about 90 weight percent water based on the total weight of the solution.

In another embodiment of the present invention, the compositions can be incorporated into products to be directly applied to the skin. Such products may include hand and body lotions as well as various types of soaps. The urease inhibiting lotion or soaps should contain an amount of *yucca* extract sufficient to provide urease inhibiting activity. A suitable amount of *yucca* extract for incorporation into lotions is at least about 0.001 weight percent, and more desirably at least about 0.01 weight percent based on the total weight of the lotion. Further, the amount of *yucca* extract should be small enough to prevent undesirable coloration of the lotion. Desirably, the amount of *yucca* extract is less than about 1.0 weight percent based on total weight of the lotion. Although other *yucca* extracts may be used without departing from the scope of the present invention, in one embodiment the *yucca* extract comprises *Yucca schidigera*, and more particularly, a *Yucca schidigera* solution sold under the trade designation *Yucca* 70 by Sher-Mar Enterprises.

For soaps, a suitable amount of *yucca* extract is at least about 0.001 weight percent, and more desirably at least about 0.01 weight percent based on the total weight of the soap. Further, the amount of *yucca* extract should be small enough to prevent undesirable coloration of the soap. Desirably, the amount of *yucca* extract is less than about 1.0 weight percent based on total weight of the soap. Although other *yucca* extracts may be used without departing from the scope of the present invention, in one embodiment the *yucca* extract comprises *Yucca schidigera*, and more particularly, a *Yucca schidigera* solution sold under the trade designation *Yucca* 70 by Sher-Mar Enterprises.

The urease inhibiting soaps and lotions of the present invention may also contain a variety of other components which may assist in providing the desired cleaning and urease inhibiting properties. For example, the soaps or lotions may also contain an alcohol such as ethyl alcohol, isopropyl alcohol, propyl alcohol, or mixtures of ethyl and isopropyl alcohols. Also, the lotions and soaps may contain water, emollients, other surfactants, preservatives, chelating agents, pH buffers, fragrances, urease inhibiting actives, or combinations or mixtures thereof. Typically, the lotions and soaps will contain a high percentage of water to reduce the possibility of skin irritation.

In another embodiment, the urease inhibiting compositions of the present invention incorporating a urease inhibiting agent can be incorporated into or onto a cellulosic web substrate such as facial tissue, bathroom tissue, feminine care product, hand towels, surgical drapes, gowns, bedsheets, pillowcases and the like. In this embodiment, the substrate will typically contain at least about 0.001 weight percent, and more desirably at least about 0.01 weight percent based on the dry weight of the substrate. Further, the amount of *yucca* extract should be small enough to prevent undesirable coloration of the substrate. Desirably, the amount of *yucca* extract is less than about 1.0 weight percent based on total weight of the substrate. Although other *yucca* extracts may be used without departing from the scope of the present invention, in one embodiment the *yucca* extract comprises *Yucca schidigera*, and more particularly, a *Yucca schidigera* solution sold under the trade designation *Yucca* 70 by Sher-Mar Enterprises. It is envisioned that the composition may be applied to at least one of the outer faces of the sheet by a conventional process such as printing or coating. Alternatively, the composition may be held within the sheet between its outer faces.

As will be appreciated by those skilled in the art, the previously described urease inhibiting compositions may be used to inhibit production of ammonia from urine such as occurs when urine is held adjacent a user's skin by an article such as a diaper, training pants, other child care products, other infant care products, adult care products and feminine care products. The compositions are applied to an area of the wearer's skin. As will be appreciated by those skilled in the art, the compositions may applied to the skin by any conventional method such as being applied directly to the skin as a lotion or indirectly applied to the skin during use of a product (e.g., as a residue of soap or from a wipe). Although the compositions may be applied in other concentrations without departing from the scope of the present invention, in one embodiment at least about 0.001 gram per square centimeter of *yucca* extract is applied to the area of the user's skin.

The present invention is illustrated by the following examples which are merely for the purpose of illustration and is not to be regarded as limiting the scope of the invention or manner in which it may be practiced.

EXAMPLE 1

Various commercially available *yucca* extracts used for animal feed supplements were tested to determine their urease inhibiting efficacy. Two milliliters (ml) of the respective *yucca* extract, 18 ml of urine and 2 ml of jack bean urease (10 milligrams/milliliter (mg/ml)) were placed in a 50 ml conical tube. The jack bean urease was obtained from Sigma Chemical Company of St. Louis, Mo., and identified as U-4002. The final concentration of jack bean urease used was 0.91 mg/ml (1.0 mg jack bean urease=1000 U). The tube was capped and the contents vigorously mixed with a vortex. After a two hour incubation period at 25 degrees Celsius, the ammonia in gas phase above the mixture was analyzed using a Gastec® ammonia detection tube available from Gastec Corporation of Ayase-shi Kanagawa-ken, Japan. A control mixture containing 2 ml of de-ionized water, 18 ml of urine and 2 ml of jack bean urease was also analyzed.

Four *yucca* extracts which were tested included 100% pure *Yucca schidigera* powder sold under the trade designation Desert Pure *Yucca* by Sher-Mar Enterprises of Poway, Calif., a *Yucca schidigera* solution sold under the trade designation *Yucca* 70 by Sher-Mar Enterprises, 50% food grade *yucca* powder sold under the product code YUCEXT50 by Garuda International, Inc. of Lemon Cove, Calif., and a *yucca* powder sold under the trade designation Dinase-30-dry by Diversified Nutri-Agri Technologies, Inc. of Gainesville, Ga. The Desert Pure *Yucca* and the Dinase-30-dry *yucca* powders exhibited low apparent urease inhibiting activity. The 50% food grade *yucca* exhibited medium apparent urease inhibiting activity, and the *Yucca* 70 exhibited high apparent urease inhibiting activity. Specific results are shown in Table 1.

TABLE 1

| *Yucca* Extract | Extract Concentration | Ammonia Measured (ppm) | % Inhibition of Released Ammonia |
|---|---|---|---|
| None | — | 780 | — |
| Dinase-30-dry | 0.9 mg/ml | 620 | 20.5 |
| Yucca 70 | 9.1 % | 130 | 83.3 |
| 100% pure *Yucca schidigera* powder | 0.9 mg/ml | 740 | 5.1 |
| 50% food grade *yucca* powder | 0.5 mg/ml | 600 | 23.1 |

EXAMPLE 2

Various concentrations of *Yucca schidigera* extract were studied to determine their urease inhibiting efficacy. An amount of a *Yucca schidigera* solution sold under the trade designation *Yucca* 70 by Sher-Mar Enterprises was thoroughly mixed in a vortex with 18 ml of urine and 2 ml of jack bean urease. After a 2 hour incubation period at 25 degrees Celsius, the resulting mixture was analyzed with an ammonia detection tube. A control mixture containing only 18 ml of urine, 2 ml of de-ionized water and 2 ml of jack bean urease was also analyzed.

The results of the mixtures containing the *yucca* extract were compared to the control mixture. The final concentrations of the *yucca* extract analyzed were zero weight percent per volume (control mixture), 0.9 percent, 4.6 percent, and 9.1 percent. The 0.9 percent mixture containing 6.3 milligrams of *yucca* extract solids per milliliter of urine demonstrated about 54 percent reduction in gas phase ammonia from the control mixture. The 4.6 percent mixture containing 31.5 milligrams of *yucca* extract solids per milliliter of urine and the 9.1 percent mixture containing 63 milligrams of *yucca* extract solids per milliliter of urine demonstrated more than 90 percent reduction in gas phase ammonia from the control mixture. Specific results are shown in Table 2.

TABLE 2

| *Yucca*-70 Concentration (%) | Ammonia Measured (ppm) | % Inhibition of Released Ammonia |
|---|---|---|
| 0 | 610 | — |
| 0.9 | 283 | 53.6 |
| 4.6 | 38 | 93.8 |
| 9.1 | 53 | 91.3 |

EXAMPLE 3

This Example is similar to Example 2 except that *Proteus mirabilis* was used instead of jack bean urease. Various concentrations of *Yucca schidigera* extract were studied to determine their efficacy for inhibiting this type of urease.

*Proteus mirabilis* (ATCC 29906) bacteria were recovered from frozen state by growing the appropriate bacterial coated MicroBank Bead (available from Pro Lab, Inc. of Austin, Tex.) in 10 ml of trypticase soy broth (TSB) (available from Difco of Ann Arbor, Mich.) in a 15 ml sterile loosely tightened screw capped conical tube overnight at 37 degrees Celsius. The tube was held stationary. Upon observation of turbidity, the bacterial suspension was checked for purity by isolation plate and Gram stain. Once determined that the isolate was *Proteus mirabilis*, a colony from the isolation plate was transferred to 10 ml of TSB in a 15 ml sterile screw capped conical tube and incubated overnight at 37 degrees Celsius under facultative conditions. Bacterial suspension from this overnight TSB culture was used.

An amount of a *Yucca schidigera* solution sold under the trade designation *Yucca* 70 by Sher-Mar Enterprises was thoroughly mixed in a vortex with 18 ml of urine and 2 ml of *Proteus mirabilis* prepared as described above. After a 22 hour incubation period at 37 degrees Celsius, the resulting mixture was analyzed with an ammonia detection tube and pH paper (available from Sigma Chemical Company of St. Louis, Mo.). A control mixture containing only 18 ml of urine, 2 ml of deionized water and 2 ml of *Proteus mirabilis* was also analyzed.

The results of the mixtures containing the *yucca* extract were compared to the control mixture. The final concentrations of the *yucca* extract analyzed were zero weight percent per volume (control mixture), 0.9 percent, 4.6 percent, and 9.1 percent. The 0.9 percent mixture containing 6.3 milligrams of *yucca* extract solids per milliliter of urine demonstrated substantially no reduction in gas phase ammonia from the control mixture and a pH about the same as the pH of the control mixture, i.e., 9.2. The 4.6 percent mixture containing 31.5 milligrams of *yucca* extract solids per milliliter of urine demonstrated about 60 percent reduction in gas phase ammonia from the control mixture and a pH of about 8.8, and the 9.1 percent mixture containing 63 milligrams of *yucca* extract solids per milliliter of urine demonstrated more than 90 percent reduction in gas phase ammonia from the control mixture and a pH of about 7.5. Specific results are shown in Table 3.

TABLE 3

| *Yucca*-70 Concentration (%) | Ammonia Measured (ppm) | % Inhibition of Released Ammonia |
|---|---|---|
| 0 | 710 | — |
| 0.9 | 850 | no effect |
| 4.6 | 285 | 59.9 |
| 9.1 | 52 | 92.7 |

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A wet wipe for controlling the production of ammonia by urine comprising:
   a flexible sheet material; and
   a composition held by the sheet comprising a *Yucca schidigera* extract.

2. A wet wipe as set forth in claim 1 wherein the sheet comprises opposite outer faces and the composition is held within the sheet between the outer faces.

3. A wet wipe as set forth in claim 1 wherein the sheet comprises opposite outer faces and the composition is applied to at least one of said outer faces.

4. A wet wipe as set forth in claim 1 wherein the conposition comprises at least about 0.001 weight percent *Yucca schidigera* extract.

5. A wet wipe as set forth in claim 4 wherein the composition comprises at least about 0.01 weight percent *Yucca schidigera* extract.

6. A wet wipe as set forth in claim 1 wherein the composition comprises less than about 1.0 weight percent *Yucca schidigera* extract.

* * * * *